United States Patent [19]
Wampler, III

[11] Patent Number: 5,703,359
[45] Date of Patent: Dec. 30, 1997

[54] COMPOSITE MEMBRANE AND SUPPORT ASSEMBLY

[75] Inventor: Francis M. Wampler, III, Syracuse, N.Y.

[73] Assignee: Leybold Inficon, Inc., East Syracuse, N.Y.

[21] Appl. No.: 681,945

[22] Filed: Jul. 29, 1996

[51] Int. Cl.$^6$ .......................... H01J 49/04; B01D 69/10
[52] U.S. Cl. ........................ 250/288; 96/11; 73/864.81
[58] Field of Search ..................... 250/288; 73/864.81; 96/11

[56] References Cited

U.S. PATENT DOCUMENTS

| | | | |
|---|---|---|---|
| 3,398,505 | 8/1968 | Llewellyn | 55/16 |
| 3,662,520 | 5/1972 | Saunders | 96/10 |
| 4,134,742 | 1/1979 | Schell | 55/16 |
| 4,769,263 | 9/1988 | Bitter | 428/36 |
| 4,791,292 | 12/1988 | Cooks et al. | 250/288 |
| 4,795,559 | 1/1989 | Shinjou et al. | 427/244 |
| 4,944,996 | 7/1990 | Bauer et al. | 428/307.7 |
| 4,954,388 | 9/1990 | Mallouk et al. | 428/198 |
| 5,019,139 | 5/1991 | LaPack et al. | 55/158 |
| 5,238,568 | 8/1993 | Fely et al. | 210/490 |
| 5,275,725 | 1/1994 | Ishii et al. | 210/321.67 |
| 5,324,938 | 6/1994 | Hambitzer et al. | 250/288 |
| 5,448,062 | 9/1995 | Cooks et al. | 250/288 |

FOREIGN PATENT DOCUMENTS

| | | |
|---|---|---|
| 299276 | of 1992 | German Dem. Rep. |
| 2629719 | of 1978 | Germany |
| 4409906 | of 1994 | Germany |
| 56-158102 | of 1981 | Japan |
| 60-58211 | of 1985 | Japan |
| 61-42305 | of 1986 | Japan |
| 63-063005 | of 1988 | Japan |
| 63-213533 | of 1988 | Japan |
| 1297124 | of 1989 | Japan |
| 64-70105 | of 1989 | Japan |
| 64-80403 | of 1989 | Japan |
| 418923 | of 1992 | Japan |
| 4317730 | of 1992 | Japan |
| 6-71147 | of 1994 | Japan |
| 6000346 | of 1994 | Japan |
| 1706673 | of 1992 | U.S.S.R. |

OTHER PUBLICATIONS

LaPack, Mark Anthony, "The Theory and Practice of Membrane Extractions", PhD Thesis, Michigan State University, 1995.

Hoch, G. & Kok B, "A Mass Spectrometer Inlet System for Sampling Gases Dissolved in Liquid Phases", Archives of Biochemistry and Biophysics 101, 160–170, 1963.

Kotiaho, T., et al. "Membrane Introduction Mass Spectrometry", Analytical Chemistry, vol. 63, No. 18 — pp. 875A–883A, 1991.

Westover, L.B. et al., "Novel Mass Spectrometric Sampling Device", Analytical Chemistry, vol. 46, No. 4 — pp. 568–571, 1974.

Wong, P.S.H. et al. "On–Line, In Situ Analysis with Membrane Introduction MS", Environmental Science & Technology, vol. 29, No. 5 — pp. 215A–218A, 1995.

Grayson, M.A. & Wolf, C.J., "Two–Stage Molecular Separator for Connecting a Gas Chromatograph to a Mass Spectrometer", vol. 42, No. 3 — pp. 426–430, 1970.

Blanchard, R.D. & Hardy, J.K., "Use of a Permeation Sampler for Determination of Volatile Priority Pollutants", Analytical Chemistry, vol. 56 — pp. 1621–1624, 1984.

(List continued on next page.)

*Primary Examiner*—Jack I. Berman
*Attorney, Agent, or Firm*—Harris Beach & Wilcox, LLP

[57] ABSTRACT

For treating a fluid sample for introduction to a mass spectrometer or other appropriate use, a composite membrane and support assembly allows analytes from a sample flow to permeate through a membrane free from the undesired background matrix. The composite membrane and support assembly comprises a semipermeable membrane, a fiber member for supporting the membrane, and a rigid perforated member for supporting the membrane and the fiber support.

51 Claims, 7 Drawing Sheets

OTHER PUBLICATIONS

Greenwalt, C.C. et al. "Transmission of Organic Molecules by a Silicone Membrane Gas Chromatograph/Mass Spectrometer Interface", Analytical Chemistry, vol. 55 — pp. 468–472, 1983.

Futo, I., & Degn, H., "Effect of Sample Pressure on Membrane Inlet Mass Spectrometry". Analytica Chimica Acta, 294 pp. 177–184, 1994.

COMPOSITE MEMBRANE AND SUPPORT ASSEMBLY

FIELD OF TECHNOLOGY

The technology of this application relates generally to techniques for identifying and quantifying analytes in fluid samples, and more particularly, to a process and an apparatus for treating a fluid sample to separate and concentrate analytes via a membrane for their introduction into a chemical analyzer providing qualitative and quantitative information on the analytes.

BACKGROUND AND SUMMARY

Membranes have been employed as sample interfaces for mass spectrometers since the first application of this technology was described by G. Hoch and B. Kok, *Arch. of Biochem. and Biophys.* 101 (1963) 171. The membrane allows selective permeation of an analyte of interest from the sample on one side of the membrane to the mass spectrometer vacuum on the other side. The benefits of this mode of analyte introduction to the mass spectrometer were given by Kotiaho et al., *Anal Chem.*, 63, (1991) 875A, and included exclusion of the bulk of the liquid or gaseous sample matrix from the ion source. This results in a cleaner ion source over extended operating times and lower vacuum pumping requirements. The selective permeation of analyte relative to sample matrix components results in an enrichment of analyte to the mass spectrometer that improves detection limits as reported by Westover et al., *Anal Chem.*, 46, (1974) 568, as well as other authors.

The membrane material most commonly used for membrane introduction mass spectrometry of volatile organic compounds in water and air samples is dimethylsilicone polymer. A number of polymer materials were screened by Westover et al., *Anal Chem.*, 46, (1974) 568, including dimethylsilicone elastomer (dimethylsilicone rubber), polyethylene, regenerated cellulose, silicone polycarbonate, polypropylene, and polyethylene/vinyl acetate copolymer, for performance as interface membranes for a range of organic compounds. In the past, the reported superiority in performance of dimethylsilicone polymer has apparently discouraged active evaluation of other polymer materials for this application.

One major problem of the dimethylsilicone membranes is the incorporation of finely-divided silica to the polymer in order to improve the membrane strength. This silica contains many active silanol groups on its surface that can potentially hydrogen-bond with polar analytes and interfere with their diffusion through the membrane, according to research by Mark Anthony LaPack of Michigan State University. This results in tailing chromatographic peaks for the polar analytes in the membrane application as an interface between a gas chromatograph and mass spectrometer. It would be an advance in the art if a polymeric membrane of suitable strength, but without silica filler, could be found for use in this application.

A possible candidate for such a membrane material is a copolymer with elastomer and polycarbonate fractions, for example a silicone polycarbonate copolymer containing dimethylsilicone and polycarbonate fractions, that provides a thinner, but stronger membrane. The elastomer fraction of the copolymer provides high transmission, while the polycarbonate fraction provides higher strength. Analyte detection limits and peak shapes would be improved by the thinner membrane, while polar analyte detection limits could be improved by their enhanced surface solubility in the more polar membrane. One major problem of polycarbonate material is its susceptibility to form "pinhole" leaks at higher operating temperatures. It would be an additional advance in this analytical membrane interface technology if the silicone polycarbonate membrane could be supported in such a manner as to prevent the formation of pinhole leaks into the mass spectrometer vacuum.

Accordingly, the present invention provides, for treating a fluid sample for introduction to a mass spectrometer or other appropriate use, a composite membrane and support assembly for allowing analytes from a sample flow to selectively permeate through a membrane to the mass spectrometer. The claimed apparatus of the invention comprises a semipermeable membrane, a fiber member for supporting the membrane, and a rigid perforated member for supporting the membrane and the fiber support member.

An embodiment of the invention will generally be either a flat, curved, or tubular shaped composite membrane and support structure incorporating a copolymer membrane comprising elastomer and polycarbonate fractions, and having a first side and a second side. One anticipated embodiment can have dimethylsilicone rubber as the elastomer fraction. The first side is exposed to a sample flow at approximately atmospheric pressure, such as the effluent from a gas chromatographic column. The second side of the membrane is supported by a thin layer of inert polymer fiber material, positioned between the membrane and a second thin support layer of rigid material that has been perforated with a pattern of small holes. These small holes allow contact of the second side of the membrane with the mass spectrometer vacuum. The layer of inert fiber supplies auxiliary support to the membrane, to prevent extrusion of the membrane through the small holes in the rigid support layer due to the pressure differential on the membrane at typical operating temperatures. This auxiliary fiber support prevents "pinholes", while at the same time maximizes the membrane area exposed to vacuum and analyte flow. It would of course be desirable if a fiber could be found that would be strong enough to eliminate the need for the further support of the rigid support layer, but no appropriate fiber is known that would allow this, while still providing the advantages of the claimed invention including the rigid support layer.

The present invention is suitable, for example, for use as an interface between a gas chromatograph and a mass spectrometer used for rapid analyses of volatile compounds in field situations. When used as a membrane interface between a gas chromatograph and a mass spectrometer, the composite membrane and support assembly is held in a housing on the upstream side of a vacuum isolation valve. The membrane housing contains a cavity on the first side of the membrane that is designed to minimize unswept volume to the sample flow. Flow channels are provided through the housing walls that allow gas chromatograph effluent flow to this cavity and to allow excess flow to exit the cavity. With the solenoid valve open, and sample flow to the first side of the membrane, analytes in the sample flow permeate across the membrane and evaporate on the second side in vacuum. The permeated analytes then flow through the open vacuum isolation valve and into the mass spectrometer ion source.

BRIEF DESCRIPTION OF THE DRAWING

For a fuller understanding of the nature and objects of the invention, reference should be made to the following detailed description to be read in connection with the accompanying figures of the drawing, in which.

DETAILED DESCRIPTION

Figure 1:
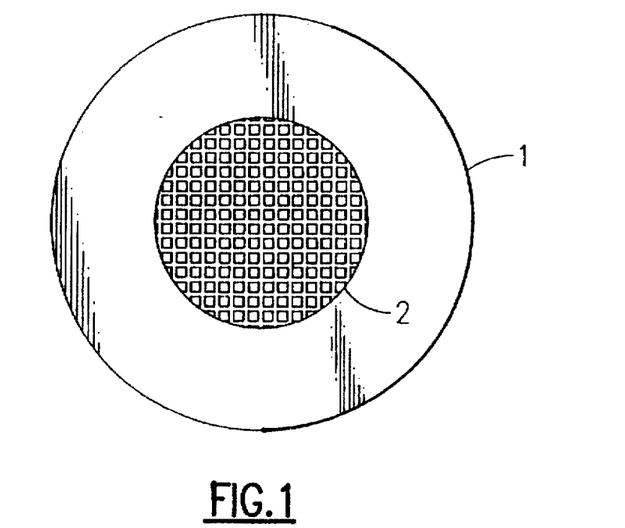
FIG. 1 is a top view of a perforated rigid membrane support disk according to a first embodiment of the invention.
Figure 2A:
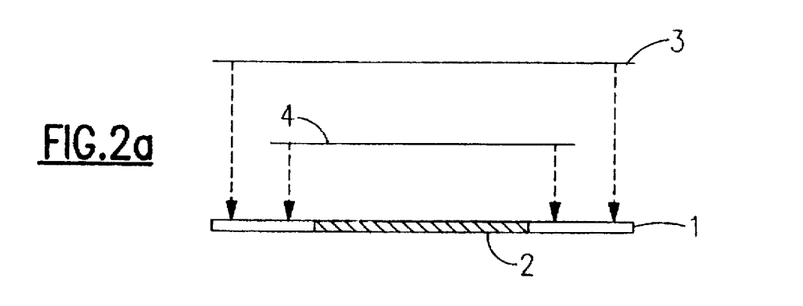
FIG. 2a is an exploded side view of a composite membrane and support assembly according to the first embodiment of the invention.
Figure 2B:
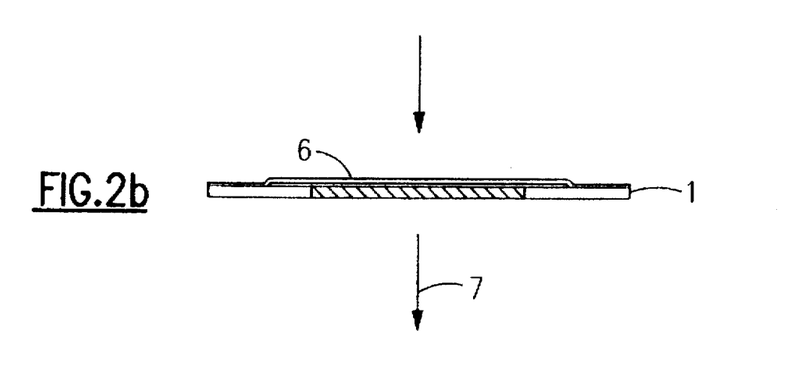
FIG. 2b is a side view of a composite membrane and support assembly according to the first embodiment of the invention.

Referring now to FIGS. 1 and 2, therein is shown a disk-shaped embodiment of a membrane and support assembly 5 according to the invention, incorporating a round sheet semipermeable membrane 3, a polymer fiber disk acting as a fiber member 4 for providing auxiliary support to the membrane 3, and a rigid perforated membrane support disk acting as rigid perforated member 1 for supporting the semipermeable membrane 3 and the fiber member 4. The auxiliary support member 4 preferably contains polyester fiber, which is an especially inert polymer fiber, but other inert fibers that do not absorb the analytes or degrade at operating conditions of the membrane and support assembly may be used. The rigid perforated member 1 is preferably stainless steel, but other suitable metal, ceramic, or polymer materials may be used. The top view of the rigid perforated member 1 shows a round area 2 containing perforations in a square mesh pattern that go completely through the rigid perforated member 1. The geometry and size of the individual perforations in area 2 may be varied so long as the membrane 3 retains its integrity at operating conditions. The membrane and support assembly 5 should be built such that the fiber member 4 is a larger diameter than the perforated area 2, and smaller in diameter than the membrane 3. The completed membrane and support assembly 5 will have the fiber member 4 centered over the perforated area 2 and held in position by the membrane 3, which seals directly to the rigid perforated member 1 around the circumference of the fiber member 4. Fluid sample flow (such as effluent from a gas chromatograph column) is applied continuously across the first side 6 (approx. atmospheric pressure) of the membrane and support assembly 5. Analytes will selectively permeate through the membrane 7 when the second side is exposed to vacuum, as through an open valve to the mass spectrometer ion source.

Figure 3:
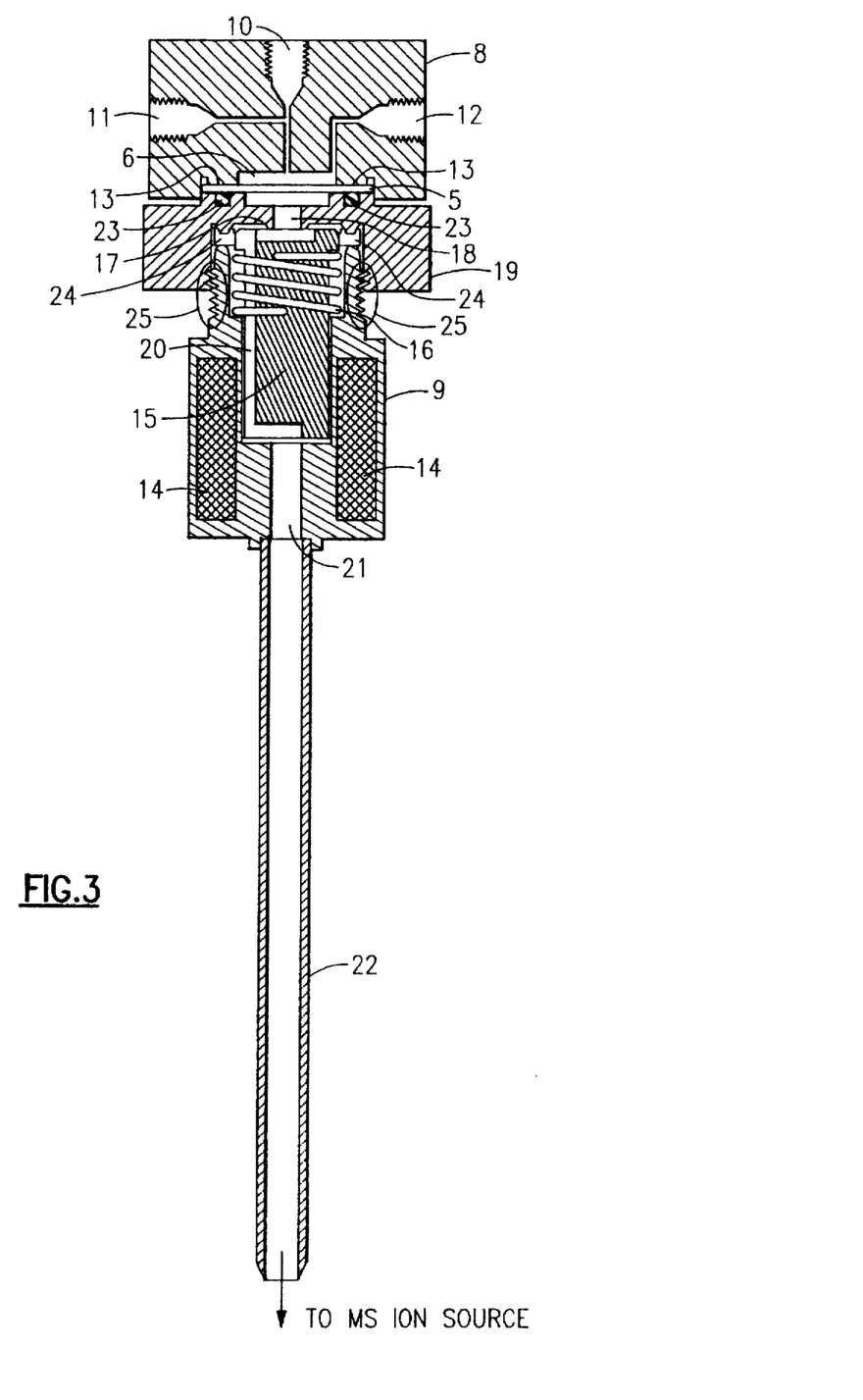
FIG. 3 is a cross-sectional schematic side view of the membrane housing and solenoid valve according to the first embodiment of the invention, incorporating the membrane and support assembly.

In FIG. 3 an embodiment of a membrane and support assembly 5 according to the invention is mounted in a membrane housing 8, on a solenoid valve 9 to allow controllable introduction of sample fluid analytes to a mass spectrometer ion source. The diagram in FIG. 3 is not intended as a detailed design drawing; for example, the valve 9 can be any type or configuration of a suitable valve that can isolate the mass spectrometer vacuum from the membrane upon demand. Likewise the design of a suitable membrane housing 8 may vary from the FIG. 3 embodiment, but will be configured to allow sample fluid flow across the first side of the membrane 6, and the excess sample fluid flow to exit the housing 8.

In operation the embodiment of FIG. 3 will permit introduction of the sample (for example, the effluent from a gas chromatograph column) through the sample port 10 of the membrane housing 8. Sample flow may also be introduced through the auxiliary port 11, or this port blocked if not in use. Sample from ports 10 and 11 flow radially across the first side of the membrane 6 of the membrane and support assembly 5, and excess sample flow exits the membrane housing 8 via the sample vent port 12. The membrane first side 6 seals directly against the membrane housing surface 13 to prevent sample flow leaks. Selected analytes from the sample flow will permeate across the membrane 3 of the membrane and support assembly 5 to the mass spectrometer ion source vacuum when the solenoid valve 9 is open. The solenoid valve 9 is opened by energizing the solenoid coil 14, which pulls down the valve plunger 15 against the tension of a spring 16 and breaks contact of the elastomer seal 17 with the opening 18 in the valve cover 19. With the valve open in this manner, the second side of the membrane 3 is exposed to vacuum (and analytes permeating the membrane can travel to the mass spectrometer ion source) via the path of the opening 18, past the elastomer seal 17, down a flow channel groove 20 in the plunger 15, and out of the valve body channel 21 through a transfer tube 22 to the mass spectrometer ion source. Leaks to vacuum by air outside the solenoid valve assembly 9 are prevented by a VITON O-ring 23 that seals between the valve cover 19 and the rigid perforated member 1 of the membrane and support assembly 5, and by a copper sealing gasket 24 between the valve cover 19 and the solenoid valve body 9. The membrane housing 8, the valve cover 19, the solenoid valve body 9 and the transfer tube are all preferably constructed of stainless steel, although other suitable materials may be used. The plunger 15 is made of magnetic iron alloy, coated with an inert fluorocarbon polymer coating. The solenoid valve body 9 and the valve cover 19 are screwed together by a threaded section 25. The membrane housing 8 and the valve cover are fastened by three screws that pass through the membrane housing and into the top of the valve cover 19 (not shown).

Since analyte permeation across the membrane is temperature dependent, the temperature of the membrane and support assembly 5 must be controlled. This may be accomplished for example, by placing the entire membrane housing/valve assembly in a constant temperature oven, or by inserting a heater cartridge/resistive temperature detector in the valve cover 19. Additional heating of the membrane housing/valve assembly when the solenoid coils 14 are energized is prevented by limiting the current level to the solenoid coils after opening. The valve 9 can be adapted from, for example, a Model 99-40-900 solenoid valve from the General Valve Corporation, Fairfield, N.J.

It should be noted that the apparatus of the present invention is not limited to the application as a GCMS interface as described above. For example, it could be used as an interface between a liquid or gaseous sample flow and a mass spectrometer ion source without the presence of some type of chromatographic instrument, as in steady-state membrane permeation experiments or flow-injection analysis. Other uses are also possible.

The membrane 3 should be a selectively permeable, non-porous polymeric membrane. The membrane 3 should be selectively permeable in that the rate of permeation of an analyte of interest across the membrane must be different from the rate of permeation of other components. Membranes of unfilled (no silica) silicone polycarbonate copolymer are preferred, as they show superior polar analyte diffusion characteristics than do silica-filled dimethylsilicone membranes. The copolymer composition of the membrane 3 may range anywhere from 10% (preferably at least 30%) polycarbonate (by weight) and 90% (preferably no more than 70%) dimethylsilicone, to 90% (preferably no more than 80%) polycarbonate and 10% (preferably at least 20%) dimethylsilicone. The membrane 3 may work with additional fractions aside from dimethylsilicone and polycarbonate, as well. Two copolymer compositions for the membrane 3 that have been shown to work well are those of General Electric's MEM-213 membrane copolymer (about 40% by weight dimethylsilicone and about 60% by weight polycarbonate), and of General Electric's MEM-973 membrane copolymer (about 30% by weight dimethylsilicone and about 70% by weight polycarbonate). In these materials the polycarbonate fraction of the copolymer imparts greater mechanical strength to the membrane without the need for silica filler. This permits a thinner membrane to be used than with pure dimethylsilicone which increases analyte permeation across the membrane 3. Additionally, the more polar polycarbonate fraction can improve polar analyte solubility on the sample side of the membrane 3, and that could also improve analyte permeation. A suitable material for the fiber member 4 for the membrane 3 material discussed above is non-woven polyester, of the type used in drain disks for liquid filtration. Such a material is supplied by Poretics, Livermore, Calif.

Figure 7:
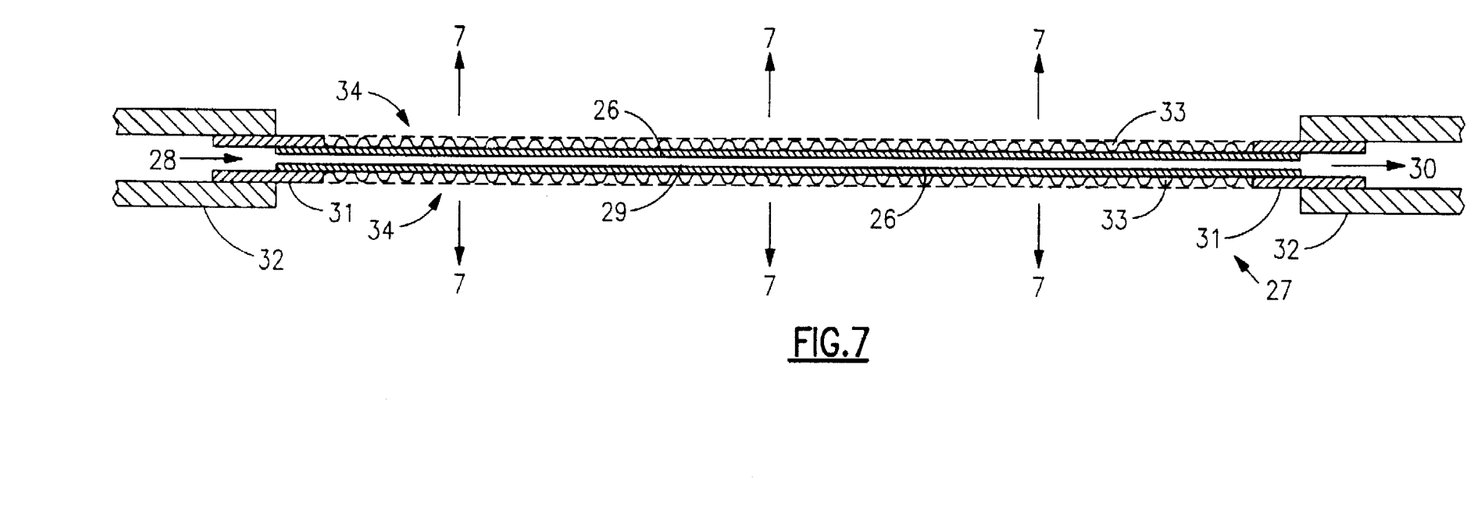
FIG. 7 is a cross-sectional schematic side view of a composite membrane and support assembly according to a second embodiment of the invention.
Figure 8:
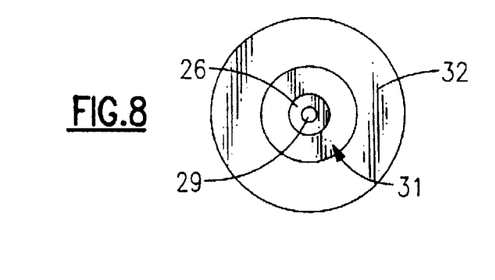
FIG. 8 is an end view of a composite membrane and support assembly according to the second embodiment of the invention.

The first embodiment shown in FIGS. 1–3 uses a flat, disk-shaped membrane and support, but geometrical shape of the elements may vary in other embodiments of the invention not illustrated, so that other physical configurations of various shapes can be used for the composite membrane and support assembly of the invention. For example, FIGS. 7 and 8 show a second embodiment 27 of the composite membrane and support assembly of the invention, with the membrane 26 configured as a tubular membrane. The sample flow would enter the membrane assembly 27 at one end 28, flow through the center bore 29 of the tubular membrane 26, and excess sample flow would exit the membrane assembly 27 at the vent exit 30. The tubular membrane 26 is affixed at both ends to support tubes 31, which are in turn concentrically mounted inside transfer tubes 32. Auxiliary support is provided to the tubular membrane 26 by a woven fiber sheath 33, and a perforated tube support 34, mounted concentrically around the tubular membrane 26, and both also affixed at the ends to the support tubes 31. The analytes from the sample flow through the membrane bore 29 would preferentially permeate the membrane 26 to the vacuum 7 leading to the mass spectrometer ion source. The membrane assembly 27 of this embodiment could be coiled into a loop configuration for insertion and operation in a modified membrane housing (similar to membrane housing 8 in FIG. 3). Other physical configurations of the invention may also be made, limited in form only by the imagination of the assembler.

For the purpose of promoting a further understanding of the invention and its features and advantages, the following discussion of experimental results is provided. That this experimental section is illustrative of one set of experimental results only, and is not meant to limit the invention as defined by the claims.

Experimental

A Perkin-Elmer QMASS 910 quadrupole mass spectrometer was used in this work. The ion source was operated at 170° C., utilizing 70 eV electron-impact ionization, at a filament current of ~250 mA. The mass spectrometer vacuum housing was pumped by a Leybold-Heraus TMP-50 turbopump throttled to a 10 liters of $N_2$ per second pumping speed by a conductance limit in the turbopump inlet. The vacuum manifold pressure was measured by a Leybold-Inficon 850-675-G1 ion gauge with readout to an IG3 vacuum gauge. The turbopump inlet and ion gauge were mounted, respectively, directly under and over the ion source region of the mass spectrometer vacuum housing. The mass spectrometer was operated in either full-scan or selected-ion monitoring mode (SIM), depending on the experiment desired.

A membrane housing/solenoid valve assembly similar to that in FIG. 3 was connected by the transfer tube 22 to an 8" long×3 mm inner diameter heated stainless steel transfer line that socketed directly into the mass spectrometer ion source. The transfer line temperature was 100° C. The temperature of the entire membrane housing/solenoid valve assembly was controlled at 60° C. inside the column oven of a Perkin-Elmer AUTOSYSTEM gas chromatograph. Sample flow to the sample port 10 of the membrane housing was supplied as the $N_2$ carrier gas effluent from a capillary gas chromatograph column. The gas chromatograph column was a 30 meter×0.32 mm inner diameter×1.0 µm film SPB-1 column (Supelco, Inc.). The $N_2$ carrier gas was ~50 cm per second linear flow and ~4.0 ml/min. volume flow at the 60° C. column operating temperature, measured at the sample vent port 12.

The sheet membranes 3 used in this work were a silicone polymer (5% phenylsilicone and 95% dimethylsilicone, by weight) filled with fumed silica to between 20–26% by weight (General Electric M100, 0.0010" thick) and a 40% dimethylsilicone and 60% polycarbonate (by weight) unfilled polymer (General Electric M213, 0.0006" thick). The M213 membrane was mounted in a membrane and support assembly 5 as in FIG. 2. The M100 membrane was mounted in the same manner, but without the fiber member 4. The auxiliary sample port 11 of the membrane housing 8 was blocked in all GCMS analyses. The sample vent port was connected via a 1/16" outer diameter×0.040" inner diameter PEEK line to exhaust in a fume hood.

Gas sample injections to the column were made from an 8-port Valco sample valve with a 100 µl stainless steel injection loop. The injector valve was also maintained at 60° C. inside the gas chromatograph column oven. Gas standard mixtures of analyte compounds were blended from UHP nitrogen and certified cylinder mixes (Scott Specialty Gases) in 12.0 liter TEDLAR gas bags (SKC Inc.). The gas bag contents were pulled through the injection loop for a minimum of 2.0 min. by the suction from a small 12 V diaphragm pump for loop conditioning prior to injection.

Results and Discussion

Figure 4A:
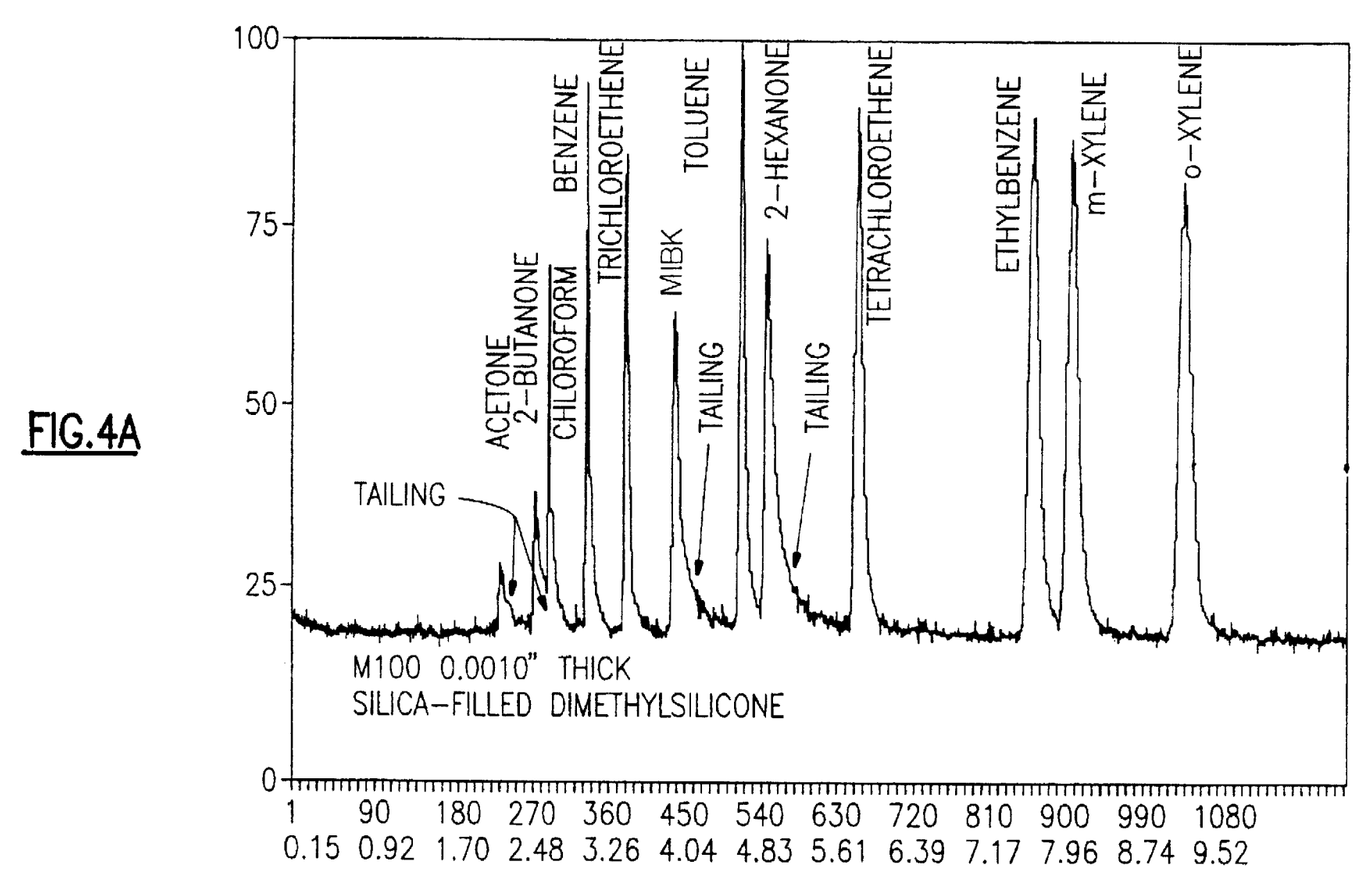
FIG. 4 shows the comparison of gas chromatograph mass spectrometer (GCMS) total ion current chromatograms for a gas standard mixture of polar and nonpolar analytes (each at 20 ppmv) comparing silica-filled dimethylsilicone and unfilled silicone polycarbonate membranes used in a GCMS membrane interface/valve assembly according to the invention.
Figure 4B:
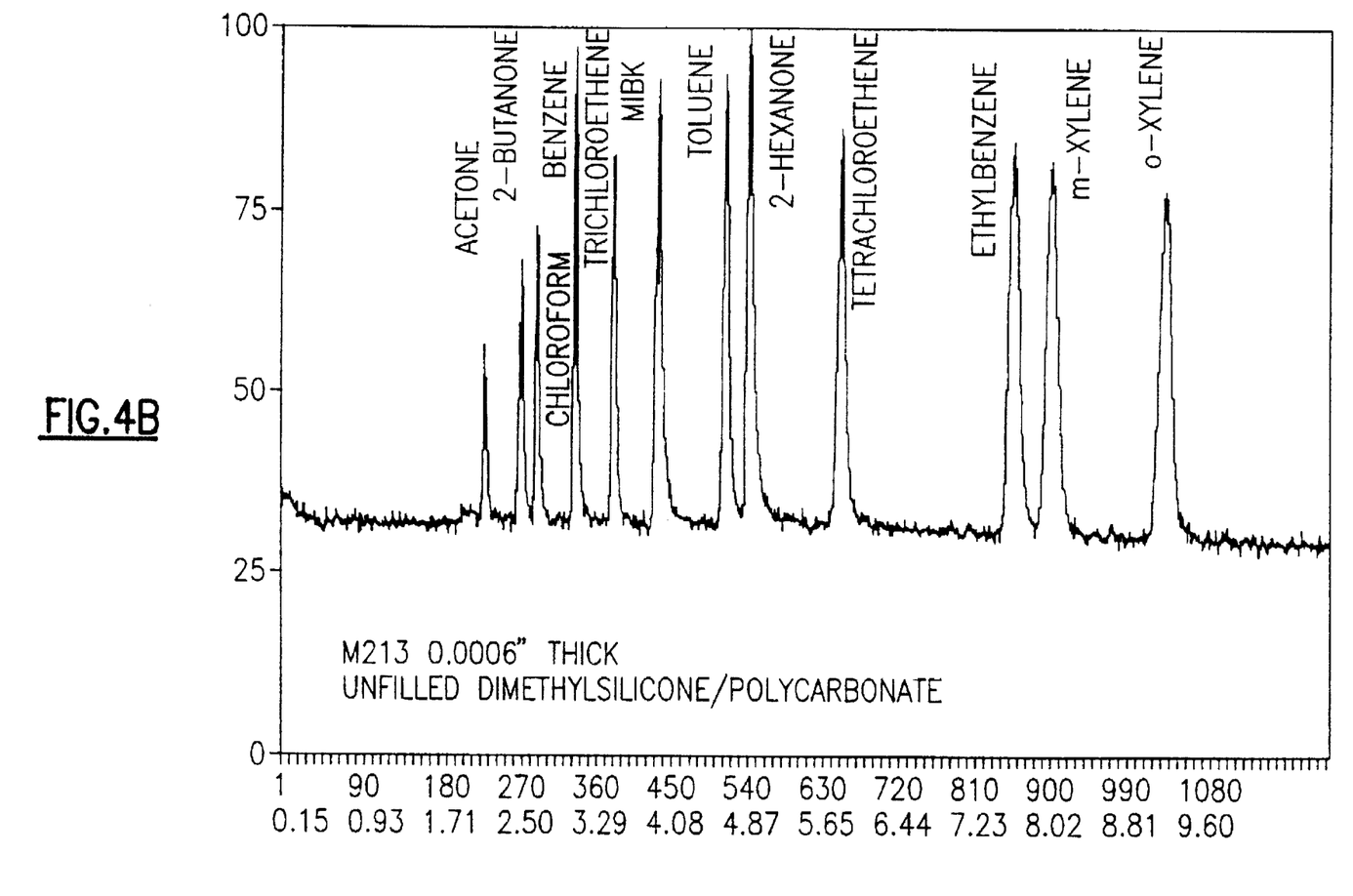

A mixture of polar and nonpolar volatile organic carbon analytes, each at the 20 ppmv level in $N_2$ were analyzed by GCMS full scan mode on both membranes for comparison of the separation and peak profiles. Mass scans from 35–285 amu were performed at 500 amu per second scan rates, producing 2 scans per second across each GCMS peak profile. A comparison of total-ion current (TIC) chromatograms with the silica-filled M100 membrane (top) and the untilled silicone polycarbonate membrane (bottom) is shown in FIG. 4. Note the pronounced peak tailing for the M100 membrane results for the polar acetone, 2-butanone, MIBK, and 2-hexanone. This peak tailing will cause interference (mass spectral overlap) for analytes eluting just after the tailing analyte peak, as is clearly shown for the 2-butanone and chloroform peaks. Signal-to-noise ratios for the tailing peaks will also be lowered, as is seen by their reduced peak heights compared to the other (non-polar) analyte peaks. This tailing is caused by the reduced diffusion of the polar analytes in the M100 material, caused by their hydrogen-bonding interactions with active silanol groups on the silica filler material, and reduction of free diffusion volume by the silica particles.

The TIC chromatogram at the bottom of FIG. 4 from the unfilled M213 membrane shows no serious peak tailing for the polar analytes. Spectral overlap of peaks here is minimized, which improves qualitative identification (note the baseline resolution of the 2-butanone and chloroform peaks). The peak heights of the polar compounds are also greatly improved compared to the non-polar analyte peaks relative to the M100 results. Note also that the non-polar analyte peak profiles are similar for both the M100 and M213 membranes for non-hydrogen bonding analytes. Peak areas of all the analytes likewise increased by 10–50% with the thinner M213 membrane, additionally improving the analyte detectability. The higher baseline TIC signal in the M213 results is due to higher $CO_2$ bleed from the silicone polycarbonate membrane that steadily reduces to very low levels after conditioning.

Residual $N_2$ carrier gas transmission through both membranes was similar, as the mass spectrometer vacuum pressure was $2.65 \times 10^{-5}$ torr for the M100 membrane, and $2.82 \times 10^{-5}$ torr for the M213 membrane.

Following the FIG. 4 results, the peak profiles for 1 ppmv levels of a number of analytes were obtained by GCMS selected-ion monitoring (GCMS SIM). Only a single selected quantion is monitored for each analyte over its gas chromatograph peak profile in GCMS SIM mode, resulting in more points per peak (9 points/sec as compared to 2 points/sec in the GCMS full-scan results). This defines the peak profile more precisely and improves signal-to-noise. The peak asymmetry ratios (PAR's) for these analyte peaks were determined at 10% peak height with the M100 and M213 membranes as described by L. R. Snyder and J. J. Kirkland, "Introduction to Modern Liquid Chromatography", 2nd Edition, (1979) p.222. The PAR's will give a more quantitative measure of peak tailing. The results are shown in TABLE 1 below.

TABLE I

GCMS SIM Mode Peak Assymmetry Values (10% Peak Height) for 60 C Membranes

| Compound | GCMS SIM ION (amu) | Peak Assymmetry Ratio (PAR)* | |
|---|---|---|---|
| | | M100 (0.0010" thick) | M213 (0.0006" thick) |
| Vinyl Chloride | 62 | 1.73 | 1.50 |
| Acetone | 43 | out of window | 1.52 |
| Carbon Disulfide | 76 | 1.75 | 1.35 |
| Vinyl Acetate | 43 | 3.61 | 1.49 |
| Chloroform | 83 | 1.90 | 1.55 |
| Benzene | 78 | 2.10 | 1.45 |
| Bromodichloromethane | 83 | 1.93 | 1.41 |
| MIBK | 43 | 5.92 | 1.59 |
| Toluene | 91 | 1.85 | 1.28 |
| Tetrachloroethene | 129 | 1.66 | 1.19 |
| Bromoform | 173 | 1.46 | 1.31 |
| Styrene | 104 | 1.46 | 1.23 |

*For nominal 1 ppmv analyte levels (except for 0.5 ppmv level of bromoform)

The polar analytes (acetone, vinyl acetate, and MIBK) showed disproportionate tailing (PAR's) in the Table 1 results for the filled M100 membrane in agreement with FIG. 4. The acetone peak tailed outside the SIM acquisition window and so its PAR could not be determined. The analyte peak PAR's for the untilled M213 membrane are consistently lower (less tailing, better peak profiles than with the filled M100 membrane. This is especially so for the polar analyte peaks, whose PAR's are much closer to those of the non-polar analyte peaks. The PAR's for the M213 membrane range from 1.19–1.59. The Snyder and Kirkland reference indicates that good quality chromatographic peaks should have PAR's<1.2. So while the M213 membrane gives better results than the M100 membrane, an even thinner M213 membrane and/or improved membrane housing design could be desirable that would not contribute tailing to peaks of PAR<1.1 expected from current gas chromatograph capillary columns.

Figure 5:
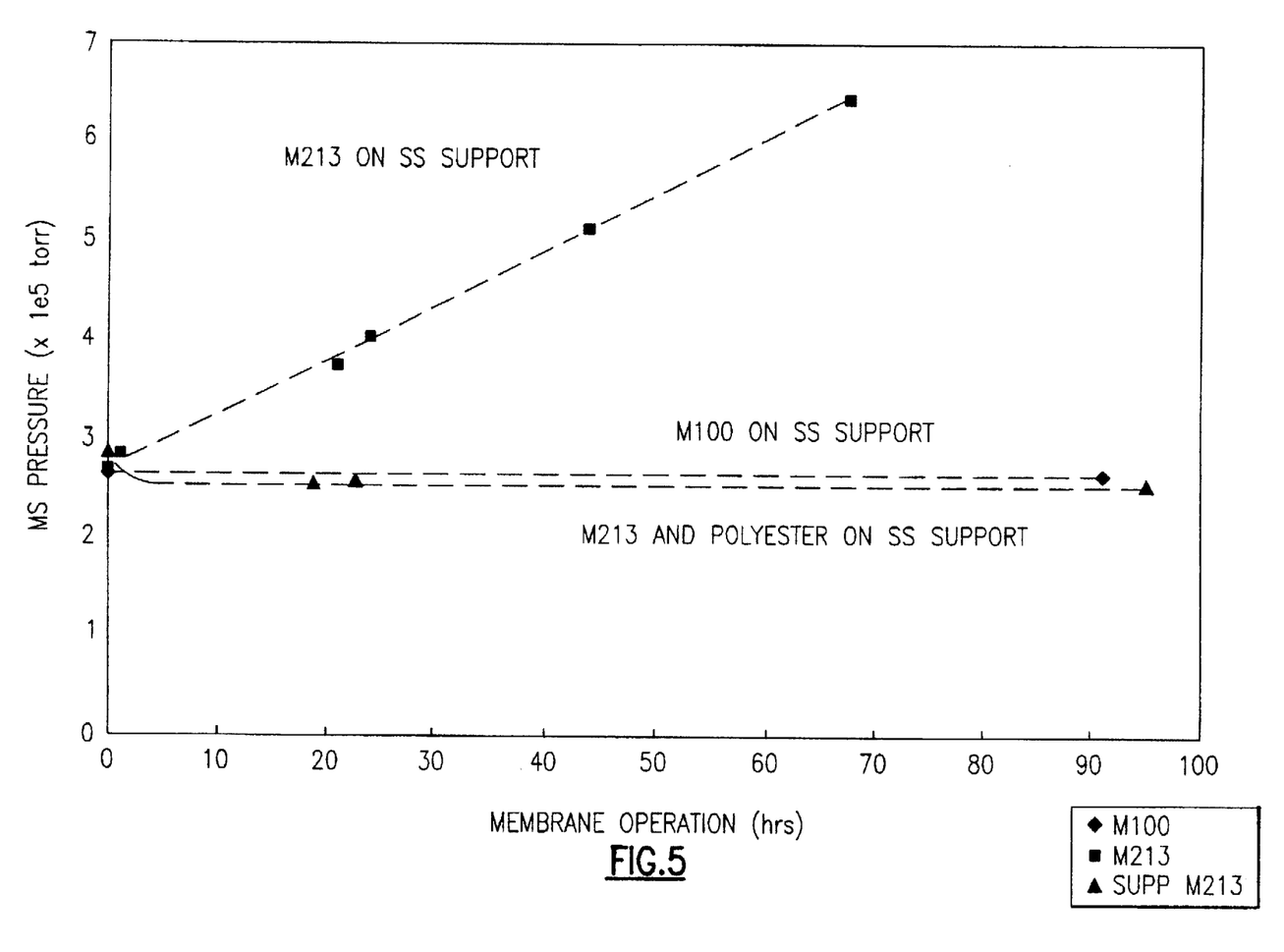
FIG. 5 shows the comparison of mass spectrometer vacuum pressure vs. time at a 60° C. silicone polycarbonate membrane temperature with and without the polymer fiber support member, and also a dimethylsilicone membrane containing silica filler and having no polymer support member, at 60° C.

One aspect of major importance for the membrane is long-term stability of the membrane under temperature and pressure differentials of operation. The M100 and M213 membranes were evaluated for stability over an approximate 90 hr. time period at 60° C., and 1 atm. pressure differential. The M213 membrane was evaluated with and without the polyester fiber member 4. The results of this study are shown in FIG. 5. Note that both the silica-filled M100 membrane and the untilled M213 membrane (incorporating the fiber member 4) produce a stable mass spectrometer pressure between $2.5 \times 10^{-5}$ and $2.8 \times 10^{-5}$ torr for up to 95 hrs. at operating conditions. Additional work has shown the M213 membrane with the polyester fiber member 4 to be stable at $2.7 \times 10^{-5}$ torr for over two weeks. If the M213 membrane is mounted directly to the stainless steel perforated member 1, an immediate and linear pressure rise is observed as shown in FIG. 5 (M213 on SS support) that leads to membrane failure within 72 hours. This pressure increase is a result of extrusion of the membrane 3 through the perforations 2 in the rigid perforated member 1. As the membrane extrudes, it gets thinner until rupture occurs.

The FIG. 5 results show that the auxiliary polyester fiber member 4 is necessary for mechanical support of the unfilled M213 membrane. Of course, any non-porous semipermeable membrane must be free of pinholes or other imperfections when mounted on the membrane and support assembly 5. The membrane and support assembly should preferably not be operated at temperatures above 70° C. (preferably not above 60° C.), or at pressure differentials much in excess of 1 atmosphere (certainly not more than 1.5 atmosphere), lest rupture occur. Exposure of the silicone polycarbonate M213 membrane to continuous high vapor concentrations of methylene chloride (a known solvent for the membrane polymer) for extended periods has shown no degradation of the membrane.

Figure 6:
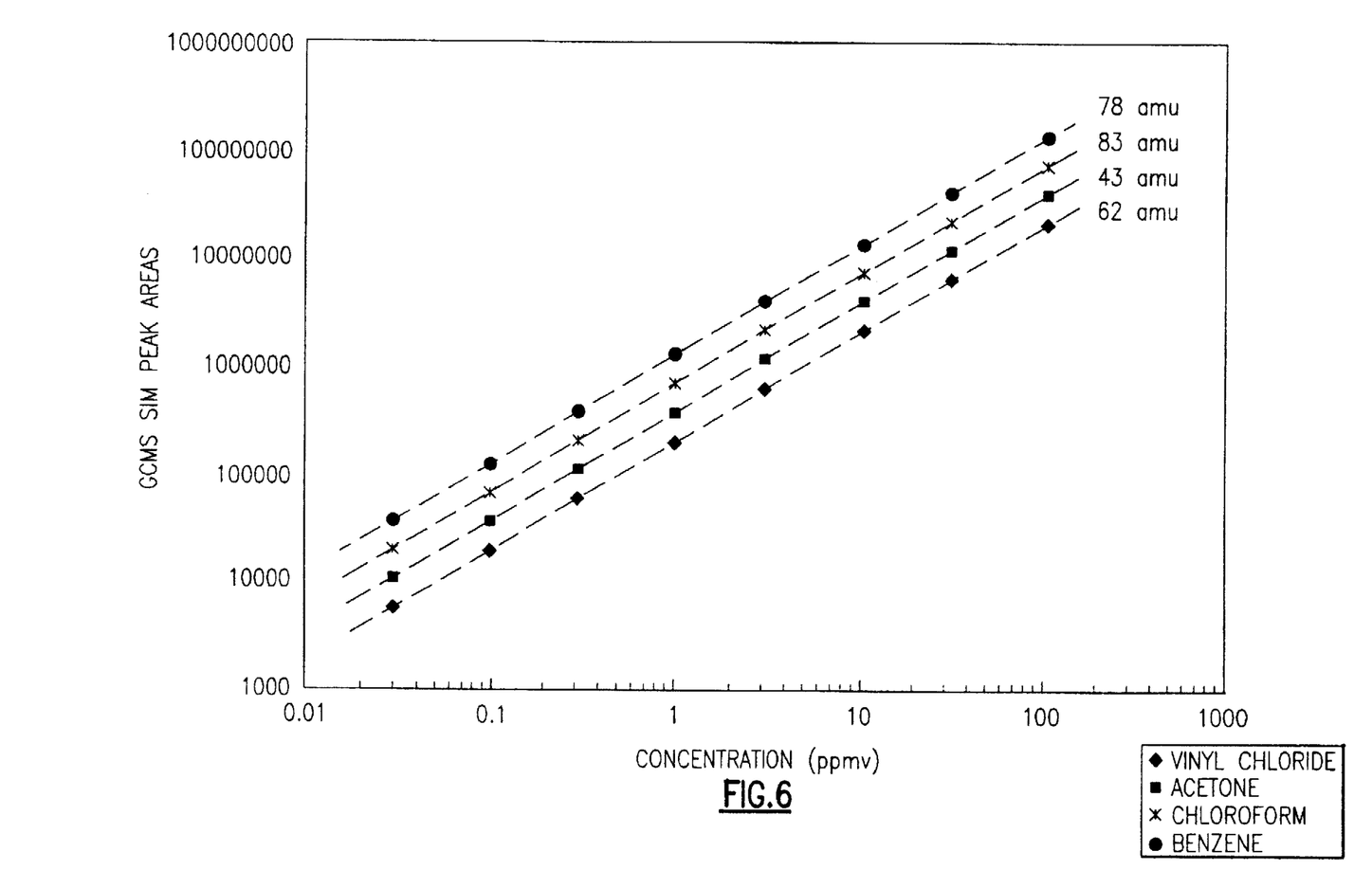
FIG. 6 shows GCMS SIM calibration plots at 30 ppbv to 100 ppmv analyte levels for a number of volatile organic analytes in nitrogen using the silicone polycarbonate membrane interface.

The linear dynamic range of analyte concentrations that can be measured with the membrane interface, and precision of such measurements is also of importance to the analyst. The plots in FIG. 6 show quantion peak area vs. concentration data for a number of analytes at 30 ppbv to 100 ppmv levels in nitrogen by GCMS SIM analysis, utilizing the M213 membrane. Note the excellent linearity of the data over this concentration range down to the region of the limit of detection for these compounds. The correlation coefficients for all these plots were 0.9999 or better. The percentage relative deviation about the mean of duplicate determinations for the analyte quantion peak areas (with the exception of the lower acetone concentrations) was less than 4.0%.

All publications cited herein, so far as they are indicative of the level of ordinary skill in the art, are hereby incorporated herein by reference.

While the present invention has been particularly shown and described with reference to the embodiments illustrated in the drawing, it will be understood by one skilled in the art that various changes in detail may be effected therein without departing from the spirit and scope of the invention as defined by the claims.

I claim:

1. A composite membrane and support assembly, comprising:

a semipermeable membrane;

a fiber member for supporting the semipermeable membrane, and;

a rigid perforated member for supporting the semipermeable membrane and the fiber member.

2. The composite membrane and support assembly recited in claim 1, wherein said semipermeable membrane comprises a silicone polycarbonate copolymer containing a silicone fraction ranging from 10% to 90%, by weight, of said silicone polycarbonate copolymer.

3. The composite membrane and support assembly recited in claim 2, wherein said semipermeable membrane comprises no silica filler.

4. The composite membrane and support assembly recited in claim 2, wherein said fiber member comprises essentially inert polymer fiber.

5. The composite membrane and support assembly recited in claim 2, wherein said fiber member comprises polyester fiber.

6. The composite membrane and support assembly recited in claim 2, wherein said semipermeable membrane is a semipermeable sheet membrane.

7. The composite membrane and support assembly recited in claim 2, wherein said semipermeable membrane is a semipermeable tube membrane.

8. The composite membrane and support assembly recited in claim 1, wherein said semipermeable membrane comprises a silicone polycarbonate copolymer containing a silicone fraction ranging from 20% to 70%, by weight, of said silicone polycarbonate copolymer.

9. The composite membrane and support assembly recited in claim 1, wherein said semipermeable membrane comprises a silicone polycarbonate copolymer containing a silicone fraction ranging from 25% to 35%, by weight, of said silicone polycarbonate copolymer.

10. The composite membrane and support assembly recited in claim 1, wherein said semipermeable membrane comprises a silicone polycarbonate copolymer containing a silicone fraction ranging from 35% to 45%, by weight, of said silicone polycarbonate copolymer.

11. The composite membrane and support assembly recited in claim 1, wherein said semipermeable membrane comprises an elastomer fraction ranging from 10% to 90%, by weight, of said semipermeable membrane.

12. The composite membrane and support assembly recited in claim 11, wherein said semipermeable membrane comprises a silicone polycarbonate copolymer containing no silica filler.

13. The composite membrane and support assembly recited in claim 11, wherein said fiber member comprises essentially inert polymer fiber.

14. The composite membrane and support assembly recited in claim 11, wherein said fiber member comprises polyester fiber.

15. The composite membrane and support assembly recited in claim 11, wherein said semipermeable membrane is a semipermeable sheet membrane.

16. The composite membrane and support assembly recited in claim 11, wherein said semipermeable membrane is a semipermeable tube membrane.

17. The composite membrane and support assembly recited in claim 1, wherein said semipermeable membrane comprises an elastomer fraction ranging from 20% to 70%, by weight, of said semipermeable membrane.

18. The composite membrane and support assembly recited in claim 1, wherein said semipermeable membrane comprises an elastomer fraction ranging from 25% to 45%, by weight, of said semipermeable membrane.

19. The composite membrane and support assembly recited in claim 1, wherein said semipermeable membrane comprises a polycarbonate fraction ranging from 10% to 90%, by weight, of said semipermeable membrane.

20. The composite membrane and support assembly recited in claim 19, wherein said semipermeable membrane comprises a silicone polycarbonate copolymer containing no silica filler.

21. The composite membrane and support assembly recited in claim 19, wherein said fiber member comprises essentially inert polymer fiber.

22. The composite membrane and support assembly recited in claim 19, wherein said fiber member comprises polyester fiber.

23. The composite membrane and support assembly recited in claim 19, wherein said semipermeable membrane is a semipermeable sheet membrane.

24. The composite membrane and support assembly recited in claim 19, wherein said semipermeable membrane is a semipermeable tube membrane.

25. The composite membrane and support assembly recited in claim 1, wherein said semipermeable membrane comprises a polycarbonate fraction ranging from 30% to 80%, by weight, of said semipermeable membrane.

26. The composite membrane and support assembly recited in claim 1, wherein said semipermeable membrane comprises a polycarbonate fraction ranging from 55% to 75%, by weight, of said semipermeable membrane.

27. The composite membrane and support assembly recited in claim 1, wherein said semipermeable membrane comprises a silicone polycarbonate copolymer containing a silicone fraction ranging from 10% to 90%, by weight, of said silicone polycarbonate copolymer, and a polycarbonate fraction ranging from 10% to 90%, by weight, of said semipermeable membrane.

28. The composite membrane and support assembly recited in claim 1, wherein said semipermeable membrane comprises an elastomer fraction ranging from 10% to 90%, by weight, of said semipermeable membrane, and a polycarbonate fraction ranging from 10% to 90%, by weight, of said semipermeable membrane.

29. The composite membrane and support assembly recited in claim 1, wherein said semipermeable membrane comprises
   a silicone polycarbonate copolymer containing a silicone fraction ranging from 20% to 70%, by weight, of said silicone polycarbonate copolymer, and
   a polycarbonate fraction ranging from 30% to 80%, by weight, of said semipermeable membrane.

30. The composite membrane and support assembly recited in claim 1, wherein said semipermeable membrane comprises
   an elastomer fraction ranging from 20% to 70%, by weight, of said semipermeable membrane, and
   a polycarbonate fraction ranging from 30% to 80%, by weight, of said semipermeable membrane.

31. The composite membrane and support assembly recited in claim 1, wherein said semipermeable membrane comprises a silicone polycarbonate copolymer containing no silica filler.

32. The composite membrane and support assembly recited in claim 1, wherein
   said semipermeable membrane comprises a silicone polycarbonate copolymer containing no silica filler, and
   said fiber member comprises essentially inert polymer fiber.

33. The composite membrane and support assembly recited in claim 1, wherein
   said semipermeable membrane comprises a silicone polycarbonate copolymer containing no silica filler, and
   said fiber member comprises polyester fiber.

34. The composite membrane and support assembly recited in claim 1, wherein
   said semipermeable membrane comprises a silicone polycarbonate copolymer containing no silica filler, and
   said semipermeable membrane is a semipermeable sheet membrane.

35. The composite membrane and support assembly recited in claim 1, wherein
   said semipermeable membrane comprises a silicone polycarbonate copolymer containing no silica filler, and
   said semipermeable membrane is a semipermeable tube membrane.

36. The composite membrane and support assembly recited in claim 1, wherein said fiber member comprises essentially inert polymer fiber.

37. The composite membrane and support assembly recited in claim 1, wherein
   said fiber member comprises essentially inert polymer fiber, and
   said semipermeable membrane is a semipermeable sheet membrane.

38. The composite membrane and support assembly recited in claim 1, wherein
   said fiber member comprises essentially inert polymer fiber, and
   said semipermeable membrane is a semipermeable tube membrane.

39. The composite membrane and support assembly recited in claim 1, wherein said fiber member comprises polyester fiber.

40. The composite membrane and support assembly recited in claim 1, wherein
   said fiber member comprises polyester fiber, and
   said semipermeable membrane is a semipermeable sheet membrane.

41. The composite membrane and support assembly recited in claim 1, wherein
   said fiber member comprises polyester fiber, and
   said semipermeable membrane is a semipermeable tube membrane.

42. The composite membrane and support assembly recited in claim 1, wherein said semipermeable membrane is a semipermeable sheet membrane.

43. The composite membrane and support assembly recited in claim 1, wherein said semipermeable membrane is a semipermeable tube membrane.

44. The composite membrane and support assembly recited in claim 1, wherein said semipermeable membrane comprises a copolymer membrane.

45. The composite membrane and support assembly recited in claim 1, wherein said semipermeable membrane is a copolymer membrane.

46. A method for obtaining analytes from an analyte-containing fluid sample, comprising the steps of:
   exposing the analyte-containing fluid sample to a first side of a composite membrane and support assembly comprising a semipermeable membrane, a fiber member supporting the semipermeable membrane, and a rigid perforated member supporting said semipermeable membrane and said fiber support; and
   accepting analytes that have permeated through the semipermeable membrane, the fiber member, and the rigid perforated member, from a second side of the composite membrane and support assembly.

47. The method as recited in claim 46, wherein said analytes in said analyte-containing fluid include at least one organic compound of the group of aromatics, aliphatics, halogenated hydrocarbons, and sulfides.

48. The method as recited in claim 46, wherein said analytes in said analyte-containing fluid include at least one polar organic compound of the group of ketones, aldehydes, esters, alcohols, ethers, carboxylic acids, phenols, amines, nitro compounds, and epoxides.

49. The method as recited in claim 46, wherein said analytes in said analyte-containing fluid include a volatile organometallic compound.

50. The method as recited in claim 46, further comprising the steps of:
   keeping the temperatures of said analyte-containing fluid sample and of said semipermeable membrane below 70° C.; and
   keeping the pressure differential between said first and second sides of the composite membrane and support assembly below 1.5 atmosphere.

51. An analyte introducing device for allowing analytes from a fluid sample to be introduced to an ion source chamber of a mass spectrometer, comprising:
   a composite membrane and support assembly comprising a semipermeable membrane, a fiber member for supporting the semipermeable membrane, and a rigid perforated member for supporting the semipermeable membrane and the fiber member;
   a passage through which the fluid sample can flow past a first side of the composite membrane and support assembly; and
   a valve for alternately isolating a second side of the composite membrane and support assembly from, and exposing the second side of the composite membrane and support assembly to, a vacuum filled transfer passage.

* * * * *